(12) United States Patent
Cid et al.

(10) Patent No.: US 8,637,692 B2
(45) Date of Patent: Jan. 28, 2014

(54) PROCESS FOR PREPARATION OF 1,2-DIAMINO-CYCLOHEXANE-PLATINUM (II) COMPLEXES

(75) Inventors: Néstor Pablo Cid, Buenos Aires (AR); Miguel Julio Novas, Buenos Aires (AR); Agustin Alfredo Tomei, Buenos Aires (AR)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 13/376,791

(22) PCT Filed: Jun. 22, 2010
(Under 37 CFR 1.47)

(86) PCT No.: PCT/EP2010/003753
§ 371 (c)(1),
(2), (4) Date: Oct. 8, 2012

(87) PCT Pub. No.: WO2010/149337
PCT Pub. Date: Dec. 29, 2010

(65) Prior Publication Data
US 2013/0131368 A1    May 23, 2013

Related U.S. Application Data

(60) Provisional application No. 61/230,866, filed on Aug. 3, 2009.

(30) Foreign Application Priority Data

Jun. 26, 2009  (EP) .................................. 09008348

(51) Int. Cl.
*C07F 15/00*      (2006.01)
(52) U.S. Cl.
USPC .......................................... 556/137

(58) Field of Classification Search
USPC ......................................................... 556/137
See application file for complete search history.

(56) References Cited

U.S. PATENT DOCUMENTS

| | | | |
|---|---|---|---|
| 4,169,846 A | 10/1979 | Kidani et al. | |
| 5,290,961 A | 3/1994 | Okamoto et al. | |
| 5,959,133 A | 9/1999 | Ohnishi | |
| 5,998,648 A | 12/1999 | Sohn et al. | |
| 7,309,796 B2 | 12/2007 | Pepels et al. | |
| 7,351,846 B2 | 4/2008 | Zák et al. | |
| 7,872,150 B2 | 1/2011 | Kysilka et al. | |
| 2004/0186172 A1 | 9/2004 | Ibrahim | |
| 2008/0207935 A1* | 8/2008 | Maikap et al. | ................ 556/137 |
| 2010/0173988 A1 | 7/2010 | Ibrahim et al. | |

FOREIGN PATENT DOCUMENTS

| | | |
|---|---|---|
| EP | 0 356 332 A | 2/1990 |
| EP | 0 617 043 A1 | 9/1994 |
| EP | 0 881 226 A1 | 12/1998 |
| EP | 1 561 754 B1 | 8/2005 |
| EP | 1 680 434 B1 | 7/2006 |
| ES | 2 183 714 | 3/2003 |
| WO | 99/33782 A1 | 7/1999 |
| WO | 03/004505 A1 | 1/2003 |
| WO | 2007/140804 A1 | 12/2007 |

* cited by examiner

*Primary Examiner* — Porfirio Nazario Gonzalez
(74) *Attorney, Agent, or Firm* — Smith, Gambrell & Russell, LLP

(57) ABSTRACT

The present invention is directed to a manufacturing process for 1,2-diamino-cyclohexane-platinum(II) complexes, specifically to a manufacturing process for oxaliplatin.

The process is straightforward, economical and applicable to industrial production. It comprises the reaction of (DACH)$PtCl_2$ with silver sulfate ($Ag_2SO_4$) and the subsequent reaction of the resulting Pt sulfate complex (DACH)Pt(aq)$_2SO_4$ with barium oxalate ($BaC_2O_4$) or an equimolar mixture of barium hydroxide and oxalic acid to yield oxaliplatin in high purity with a low silver and low nitrate content.

13 Claims, No Drawings

PROCESS FOR PREPARATION OF 1,2-DIAMINO-CYCLOHEXANE-PLATINUM (II) COMPLEXES

The present invention relates to a method for the preparation of 1,2-diaminocyclohexane-platinum (II) complexes, in particular cis-oxalato-(trans-l-1,2-cyclohexanediamine)-platinum (II) complexes such as oxaliplatin. Furthermore, the invention relates to an oxaliplatin substance of high purity and its use as pharmacologically active compound in pharmaceutical compositions (e.g. for the treatment of cancer).

"Oxaliplatin", CAS Number [61825-94-3] is the generally used name for a Pt(II)-complex with the chemical name (SP-4-2)-[(1R,2R))-1,2-cyclohexandiamine-N,N']-[oxalato-O,O']-platinum(II). The conventional name is "cis-oxalato-(trans-l-1,2-cyclohexanediamine)-platinum (II)". Oxaliplatin is a cytostatic drug against metastatic colorectal carcinoma. Basically, the oxaliplatin complex is a mixture of 3 isomers: a cis-isomer, which is a geometrical isomer and two trans-isomers (trans-d and trans-l), which are optical isomers (enantiomers). Oxaliplatin is the pure trans-l enantiomer having the following formula:

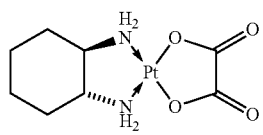

While the anti-tumor activity of cis-platinum (II) compounds was generally known, the specific Pt compound was discovered in 1976 at Nagoya University (Japan) by Professor Yoshinori Kidani (ref to U.S. Pat. No. 4,169,846). Oxaliplatin is now frequently used in cancer therapy.

The process described in U.S. Pat. No. 4,169,846 is based on the reaction of the (SP-4-2)-dichloro-[(1R,2R))-1,2-cyclohexandiamine-N,N']-platinum(II) complex, in the following abbreviated as (DACH)PtCl$_2$, in water with two equivalents of silver nitrate (AgNO$_3$), an elimination of the obtained solid phase and a subsequent reaction of the obtained [(1R,2R)-1,2-cyclohexandiamine-N,N']-platinum(II) diaquo-dinitrate (hereinafter abbreviated as (DACH)Pt(aquo)-2-dinitrate) with oxalic acid and/or its alkali metal salts. The product must be purified by recrystallisation; the final yield of the obtained oxaliplatin is usually quite low. Therefore, this general procedure is not suitable for industrial application.

Various methods for the preparation of oxaliplatin were later disclosed in the patent literature.

A major focus was on the reduction of the silver content of the oxaliplatin product to fulfil the requirements of the pharmaceutical specifications. According to the European Pharmacopeia April 2003, Annex 4.4, the silver content must be less than 5 ppm (as detected by AAS). Purification steps, which use alkaline iodides for the elimination of silver ions and other impurities from the (DACH)Pt(II) diaquo complexes were frequently reported in the state of the art.

U.S. Pat. No. 5,290,961 (and the corresponding EP 61704381) disclose a process for oxaliplatin manufacture, in which in a first step not less than two equivalents of silver are added to the compound (DACH)PtCl$_2$. Thereafter, the precipitated AgCl is removed and sodium iodide and/or potassium iodide is added to convert the unreacted (DACH)PtCl$_2$, its by-products and unreacted silver ions into their iodine compounds followed by the removal thereof. After this step, oxalic acid is added to form the oxaliplatin complex.

In WO 03/004505 A1, a similar purification step based on the addition of iodide ions is reported.

EP 1680434B1 discloses the addition of quarternary ammonium iodide compounds of the type (NR$_4$)N I for removal of trace contaminants.

EP 1561754B1 describes a preparation process for oxaliplatin using the tetra-iodo complex K$_2$PtI$_4$ as starting material for preparing the compound (DACH)PtI$_2$. This intermediate is reacted with a silver salt such as AgNO$_3$, the precipitated AgI is removed and the remaining (DACH)Pt-(aquo)-2-dinitrate complex is converted to oxaliplatin by addition of an oxalate compound.

A similar preparation method, also starting from K$_2$PtI$_4$, is disclosed in ES 2183714A1.

A drawback of the methods employing the iodide compound K$_2$PtI$_4$ as starting material is that an additional step is coming to the process (due to the preparation of the K$_2$PtI$_4$ complex from the dichloro compound K$_2$PtCl$_4$), Thus, the resulting overall procedure is time-consuming and costly.

Furthermore, the preparation methods employing iodides lead to discoloration of the product due to the formation of platinum(II) mono- and diiodo complexes. The crude oxaliplatin product must therefore be recrystallized from water.

WO 2007/140804 discloses a method for manufacture of oxaliplatin, in which a solid inert material and a solid polymeric material containing cationic exchange groups is added in the various reaction steps.

EP 881226 teaches the use of deoxygenated water and a low oxygen environment for the production of oxaliplatin. Such processes are too time-consuming and costly to employ in industrial production scale.

In summary, the presently disclosed processes for manufacture of oxaliplatin are suffering from various drawbacks and are time-consuming, lengthy and costly.

Therefore it was an objective of the present invention to provide a manufacturing process for oxaliplatin, which is quick, simple, straightforward, economical and applicable to industrial production. The process should deliver the oxaliplatin product in high yield and high purity, suitable for pharmaceutical use. Furthermore, it was an objective to provide a process, in which the individual steps employed should not require deoxygenated water or low oxygen atmosphere.

These objectives are met by the preparation method according to the claims of the present invention.

The present invention provides a process for preparing oxaliplatin (cisoxalato-(trans-l-1,2-cyclohexanediamine)-platinum-II) of the structural formula I:

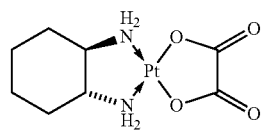

comprising the following steps:
a) reacting potassium tetrachloroplatinate (II) [K$_2$PtCl$_4$] with trans-l-1,2-cyclohexanediamine to obtain the dichloro-[(trans-l-1,2-cyclohexanediamine-N,N']-platinum(II) complex,
b) reacting the dichloro-[(trans-l-1,2-cyclohexandiamine-N,N']-platinum(II) complex with silver sulfate (Ag$_2$SO$_4$) to obtain [(trans-l-1,2-cyclohexandiamine-N,N']-platinum (II)-diaquo-sulfate and silver chloride (AgCl),
c) reacting the [(trans-l-1,2-cyclohexandiamine-N,N']-platinum(II)diaquo sulfate with barium oxalate (BaC$_2$O$_4$) to obtain oxaliplatin (cis-oxalato-(trans-l-1,2-cyclohexane-diamine)-platinum-II) and barium sulfate ($BaSO_4$).

The reaction steps a)-c) of the process of the present invention can be depicted in the following equations (1)-(3) (wherein "DACH" is the abbreviation for trans-l-1,2-cyclohexanediamine and "aq" denotes a $H_2O$ ligand in the Pt sulfate complex):

Step a): $K_2PtCl_4$+trans-l-DACH==>(DACH)$PtCl_2$ (1)

Step b): (DACH)$PtCl_2$+$Ag_2SO_4$==>
(DACH)Pt(aq)$_2SO_4$+2AgCl (2)

Step c): (DACH)Pt(aq)$_2SO_4$+$BaC_2O_4$==>
(DACH)Pt($C_2O_4$)+$BaSO_4$ (3)

In a preferred embodiment of the invention, the barium oxalate ($BaC_2O_4$) employed in step c) is added in the form of separate components to the reaction mixture. Thus it can be formed "in situ" during the reaction. In this case, the two compounds oxalic acid ($H_2C_2O_4$) and barium hydroxide (Ba(OH)$_2$) are added successively or simultaneously in stoichiometric portions (i.e. equimolar) to the reaction mixture under stirring:

Step c1): (DACH)Pt(aq)$_2SO_4$+$H_2C_2O_4$+Ba(OH)$_2$==>
(DACH)Pt($C_2O_4$)+$BaSO_4$ (3')

Thus, in a preferred embodiment, the method of the present invention provides a process for preparing oxaliplatin (cis-oxalato-(trans-l-1,2-cyclohexanediamine)-platinum-II) of the structural formula I comprising the following steps:
a) reacting potassium tetrachloroplatinate (II) [$K_2PtCl_4$] with trans-l-1,2-cyclohexanediamine to obtain the dichloro-[(trans-l-1,2-cyclohexanediamine-N,N']-platinum(II) complex,
b) reacting the dichloro-[(trans-l-1,2-cyclohexandiamine-N,N']-platinum(II) complex with silver sulfate ($Ag_2SO_4$) to obtain [(trans-l-1,2-cyclohexandiamine-N,N']-platinum(II)-diaquo-sulfate and silver chloride (AgCl),
c1) reacting the [(trans-l-1,2-cyclohexandiamine-N,N']-platinum(II)diaquo-sulfate with equimolar portions of barium hydroxide Ba(OH)$_2$) and oxalic acid ($H_2C_2O_4$) to obtain oxaliplatin (cis-oxalato(trans-l-1,2-cyclohexanediamine)-platinum-II) and barium sulfate ($BaSO_4$).

In this preferred embodiment, inexpensive starting materials can be used, which are readily available on the market.

The preparation processes of the invention may further comprise a step b') of removal of the precipitated silver chloride (AgCl) after step b) and a step c') of removal of the precipitated barium sulfate ($BaSO_4$) after steps c)/c1). In addition to these steps, further steps for removal of impurities and/or isolation and/or purification of the oxaliplatin product may be added to the process. As an example, the preparation process of the present invention may comprise the following steps:
a) reacting potassium tetrachloroplatinate (II) [$K_2PtCl_4$] with trans-l-1,2-cyclohexanediamine to obtain the dichloro-[(trans-l-1,2-cyclohexanediamine-N,N']-platinum(II) complex,
b) reacting the dichloro-[(trans-l-1,2-cyclohexandiamine-N, N']-platinum(II) complex with silver sulfate ($Ag_2SO_4$) to obtain [(trans-l-1,2-cyclohexandiamine-N,N']-platinum (II)-diaquo-sulfate and silver chloride (AgCl),
b') removal of the precipitated silver chloride (AgCl),
c)/c1) reacting the [(trans-l-1,2-cyclohexandiamine-N,N']-platinum(II)diaquo-sulfate with barium oxalate ($BaC_2O_4$) (=step c)) or with equimolar portions of barium hydroxide (Ba(OH)$_2$) and oxalic acid ($H_2C_2O_4$) (=step c1)) to obtain oxaliplatin (cis-oxalato-(trans-l-1,2-cyclohexane-diamine)-platinum-II) and barium sulfate ($BaSO_4$),
c') removal of the precipitated barium sulfate ($BaSO_4$) and
d) isolating and/or purification of the oxaliplatin product.

The present invention provides a manufacturing process for oxaliplatin, which is quick, straightforward, economical and applicable to industrial production. The process provides the oxaliplatin product in high yield and in high purity, in particular with a low silver content (<5 ppm). Compared to prior art manufacturing methods, the present process does not employ purification steps based on the addition of iodine compounds. Furthermore, the compound $K_2PtI_4$ is not used as a starting material.

In general, the present process differs in two important features from the manufacturing methods of the prior art. At first, it uses silver sulfate (instead of silver nitrate) for the preparation of the intermediate (DACH)Pt(aq)$_2$ complex in step b). Secondly, the process employs barium oxalate ($BaC_2O_4$)—or alternatively an equimolar mixture of barium hydroxide (Ba(OH)$_2$) and oxalic acid ($H_2C_2O_4$)—for the preparation of the oxaliplatin product (DACH)Pt($C_2O_4$) in step c).

The combination of these measures results in a very effective manufacturing process, allowing the removal of the ionic contaminants (barium ions and sulfate ions) from the mother liquor in the form of the practically water-insoluble $BaSO_4$. It was surprisingly found that, after the removal of the $BaSO_4$ precipitate, the oxaliplatin product can be isolated in high purity from the mother liquor by simple solvent evaporation and crystallisation.

As there are a reduced number of processing steps and washing/purification procedures employed in the process, the product yields are quite high, reaching up to 80%.

In summary, the method according to the present invention provides very pure oxaliplatin product in high yield, which can be used as a pharmacologically active compound in pharmaceutical compositions.

DETAILED DESCRIPTION OF THE INVENTION

As already mentioned, the oxaliplatin compound is a mixture of 3 isomers. Oxaliplatin consists of the pure trans-l enantiomer. In order to achieve a high optical purity of the final oxaliplatin product, a trans-l-1,2-cyclohexane-diamine [=(1R,2R)-Diaminocyclohexane (DACH)] ligand with high optical purity should be employed in the process.

Step a: Potassium tetrachloroplatinate (II) [$K_2PtCl_4$], the starting material for step a), is readily available on the market. Typically, the Pt content should be in the range of 46.0 to 47.5 wt.-% and the water content should be <1 wt. %.

The (1R,2R)-diaminocyclohexane enantiomer suitable as starting material of the present invention should have a minimum optical purity of 99.5%, the content of the trans-d (=1S, 2S) isomer should be <0.1%. Suitable DACH materials are manufactured by newly developed enantiomer separation technologies and are available from several vendors. The mixture of potassium chloroplatinate ($K_2PtCl_4$) and DACH is stirred at room temperature for a time in the range of 2 to 10 hours, preferably in the range of 4 to 8 hours. The yellow (DACH)$PtCl_2$ precipitates and can be isolated e.g. by filtration with a filter unit. This intermediate (DACH)$PtCl_2$ is washed with purified water and organic solvents such as methanol and/or acetone. Drying is performed preferably in vacuum for a period of 1 to 6 hours.

Step b): Generally, the silver sulfate employed in step b) is used in stoichiometric amounts in relation to the starting (DACH)$PtCl_2$ complex, e.g. per molar equivalent of the starting Pt complex one molar equivalent of silver sulfate is employed. The components are stirred in aqueous solution at room temperature (20° C.); the typical reaction time is in the range of 10 to 30 hours. Slightly increased reaction temperatures in the range of 30-50° C. may be used to avoid prolonged reaction times. The silver sulfate suitable for the present process should have a silver content of about 68.0 to 69.5 wt.-% Ag and a water content of <1 wt. %. Suitable products are available from different vendors.

Step c)/c1): The barium oxalate ($BaC_2O_4$) employed in step c) is commercially available or can be prepared separately prior to use in a simple reaction between equimolar amounts of barium hydroxide ($Ba(OH)_2$) and oxalic acid ($H_2C_2O_4$) in water. In case step c1) is employed, the components barium hydroxide ($Ba(OH)_2$) and oxalic acid ($H_2C_2O_4$) are added successively or simultaneously to the reaction mixture. Hereby, barium oxalate ($BaC_2O_4$) is formed "in situ" in the reaction mixture. Barium hydroxide ($Ba(OH)_2$) may be employed in its mono-hydrate or its octa-hydrate form; oxalic acid can be used pure or in its di-hydrate form. All of these starting compounds are readily available on the market.

Generally, in step c) the pH is adjusted to the range of pH=4-7, preferably to the range of pH=5-6.5 after addition of the barium oxalate ($BaC_2O_4$). In step c1), i.e. in case barium hydroxide ($Ba(OH)_2$) and oxalic acid ($H_2C_2O_4$) are added as separate compounds to the mixture, the pH is adjusted to the same pH range. Typically, steps c) and c1) are conducted at room temperature or at slightly increased reaction temperatures in the range of 30-50° C.

Steps b') and c'): The removal of the precipitated silver chloride (step b')) is performed after step b) and the removal of the precipitated barium sulfate (step c')) is conducted after step c) or step c1). These steps can be performed by use of standard separation and filtration operations known in the art. Separation and filtering equipment such as suction funnels, filter paper, filter presses, centrifuges etc. may be used. For improvement of the filtration process, aqueous suspensions of activated carbon (activated charcoal) may be spread over the filter paper prior to the start of the filtration processes. The filter cakes of precipitated AgCl (obtained in step b')) and barium sulfate (obtained in step c')) are generally analyzed by XRF (X-ray fluorescence) for platinum residues. If Pt residues are visible as defined peaks in the XRF spectrum, the corresponding filter cakes may be resuspended in purified water, stirred and filtered again. Finally the filter cakes may be collected for Pt recovery. If necessary, the filtration process may be repeated and the filtered solution containing the product (DACH)Pt($C_2O_4$) may be filtered again.

Step d): For product isolation and/or purification, the resulting aqueous solution obtained in step c) or step c1) are concentrated in a rotation evaporator (e.g. "Rotavapor") using a water-jet vacuum (10-20 Torr) at temperatures in the range of 25 to 50° C. Generally, the water is removed to almost dryness. Hereby, the oxaliplatin product crystallizes and precipitates. The resulting precipitate is isolated from the mother liquor by filtration and washed with cold, highly purified water and thereafter with acetone. Finally, the product is dried under vacuum for 1 to 5 hours.

Product Purity: Typically, in the oxaliplatin product prepared according to the present invention, the Ag content is <5 ppm, preferably <3.5 ppm (as detected by atomic absorption spectroscopy, AAS). Thus, the product fulfils the specification of the European Pharmacopeia Apr. 2003, Annex 4.4. If necessary, suitable recrystallisation steps in purified water may be added. A general advantage of the present process is that no nitrate ions ($NO_3^-$ ions) are employed. Thus, the contamination of the resulting oxaliplatin product with this ion is very low; the content of $NO_3^-$ typically is <5 ppm, preferably <1 ppm (as detected by ion chromatography). Similarly, the content of $Na^+$ and $K^+$ typically is <5 ppm, preferably <1 ppm (as detected by ion chromatography). The final oxaliplatin product prepared according to the present invention reveals a very high optical purity. The concentration of the trans-d (=1S,2S) isomer is generally <0.1%. The product fulfils the requirements of the specification of the European Pharmacopeia Apr. 2003, Annex 4.4.

As a rule, the total yield of pure product is in range of 60 to 80%, more specifically in the range of 65 to 80% (based on Pt employed in the starting material $K_2PtCl_4$). Product lumps may be de-agglomerated in a mortar. For protection against light, the product is stored in dark plastic bottles.

The following examples may illustrate the invention without narrowing its scope.

EXAMPLES

General Remarks: Deionized water is used for all steps except for the stage of washing/rinsing of the final product. Here, highly purified water having a limited bacteria content (according to European Pharmacopoeia 4) is used.

Analytical Procedures: Silver concentration is detected by AAS (Atomic absorption spectroscopy); XRF (X-ray fluorescence spectroscopy) is used for detection of residual platinum and silver contents. The alkali ions ($Na^+$, $K^+$ etc) as well as the $NO_3^-$ content are determined by ion chromatography (IC).

Example 1

Step a): Preparation of (DACH)$PtCl_2$ 106.4 g of potassium chloroplatinate $K_2PtCl_4$ (0.256 mol; Pt-content 47.0 wt.-%; corresponding to 50.0 g Pt, supplier Umicore) are placed into a 5 l polypropylene tank and dissolved in 5 l of deionized water. Thereafter, 30 g of trans-l-1, 2-cyclohexane-diamine [(R,R)-1,2-Diaminocyclohexane, CAS No. 20439-47-8], optical purity 99.5%) is added and the mixture is stirred at room temperature for 6 hours. The yellow product (DACH)$PtCl_2$ precipitates and is isolated by filtration over a filter unit. The filter cake is washed with deionized water, methanol and acetone and dried by vacuum for 4 hours. Yield >95%.

Step b): Reaction of (DACH)$PtCl_2$ with Silver Sulfate 8 l of deionized water are charged into a 20 l polypropylene tank and 81.6 g silver sulfate $Ag_2SO_4$ (0.26 mol; supplier Umicore) are added under stirring. Then, the Pt complex (DACH)$PtCl_2$ as prepared in step a), is added and the resulting suspension is stirred at room temperature for 20 hours. The precipitated AgCl is removed by filtration (step b')). Before start of filtration, a suspension of activated carbon is applied over the filter paper. The filter cake is washed with deionized water and collected for Pt recovery. The filtrate contains the (DACH)Pt(aquo)$_2$-(II)-sulfate complex, which is used in step c).

Step c1): Reaction of (DACH)Pt(aquo)$_2$(II)-Sulfate with Barium Hydroxide and Oxalic Acid The filtrate obtained from step b) (approx. 10-12 l), containing the (DACH)Pt(aquo)$_2$-(II)-sulfate complex, is placed in a 20 l polypropylene tank. Thereafter, 32.4 g of oxalic acid dihydrate ($H_2C_2O_4 \times 2\ H_2O$; 0.26 mol) and 81.6 g barium hydroxide octahydrate ($Ba(OH)_2 \cdot \times 8\ H_2O$; 0.26 mol) are added under stirring. The reaction mixture is stirred for 20 hours at room temperature. The pH of the suspension is maintained at about pH=6. Then the filtration of the precipitated $BaSO_4$ is conducted through a filter unit (step c')). Before start of filtration, a suspension of activated carbon is applied over the filter paper. The filter cake is washed with 1.5 l of deionized water and collected for Pt recovery.

The resulting solution is evaporated in a Rotavapor at 40° C. to almost dryness, whereby the oxaliplatin precipitates. The resulting precipitate is washed with 0.2-0.3 l of cold highly purified water (free of bacteria) and then with acetone. To protect the product against light, these operations are conducted under low intensity light. Finally, the product is dried under vacuum for 2 hours. The total yield of pure product is 65%.

The product is thereafter analyzed for impurities. Typically, the Ag content as detected by atomic absorption spectroscopy (AAS) is <5 ppm, preferably <3.5 ppm. If necessary, a recrystallisation step in purified water is added. In this example, the nitrate content is <1 ppm as detected by ion chromatography.

Example 2

This Example is conducted according to Example 1, however, barium oxalate ($BaC_2O_4$) is used instead of barium hydroxide and oxalic acid (i.e. step c) is employed).

Barium oxalate is prepared separately by reacting equimolar portions of oxalic acid dihydrate ($H_2C_2O_4 \times 2H_2O$) and barium hydroxide octahydrate ($Ba(OH)_2 \cdot 8H_2O$) in deionized water. After reaction, the precipitated barium oxalate is isolated by filtration and dried prior to use.

The filtrate obtained in Example 1, step b) containing the $(DACH)Pt(aquo)_2$-(II)-sulfate complex (approx. 10-12 l), is placed in a 20 l polypropylene tank. Thereafter 58.8 g of barium oxalate ($BaC_2O_4$, 0.26 mol) are added under stirring. The reaction mixture is stirred for 20 hours at room temperature. The pH of the suspension is maintained at about pH=6.

The further isolation of the product is conducted as described in Example 1.

The invention claimed is:

1. A process for preparing oxaliplatin (cis-oxalato-(trans-l-1,2-cyclohexanediamine)-platinum-II) of the structural formula I:

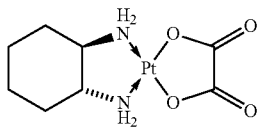

formula I comprising the following steps:
   a) reacting potassium tetrachloroplatinate (II) [$K_2PtCl_4$] with trans-l-1,2-cyclohexanediamine to obtain the dichloro-[(trans-l-1,2-cyclohexandiamine-N,N']-platinum(II) complex,
   b) reacting the dichloro-[(trans-l-1,2-cyclohexandiamine-N,N']-platinum (II) complex with silver sulfate ($Ag_2SO_4$) to obtain [(trans-l-1,2-cyclohexandiamine-N,N']-platinum(II)-diaquo sulphate and silver chloride (AgCl),
   c) reacting the [(trans-l-1,2-cyclohexandiamine-N,N']-platinum(II)-diaquo-sulfate with barium oxalate ($BaC_2O_4$) to yield oxaliplatin (cis-oxalato-(trans-l-1,2-cyclohexane-diamine)-platinum-II) and barium sulfate.

2. A process for preparing oxaliplatin (cis-oxalato-(trans-l-1,2-cyclohexanediamine)-platinum-II) of the structural formula I comprising the following steps:
   a) reacting potassium tetrachloroplatinate (II) [$K_2PtCl_4$] with trans-l-1,2-cyclohexanediamine to obtain the dichloro-[(trans-l-1,2-cyclohexane-diamine-N,N']-platinum (II) complex,
   b) reacting the dichloro-[(trans-l-1,2-cyclohexandiamine-N,N']-platinum(II) complex with silver sulfate ($Ag_2SO_4$) to obtain [(trans-l-1,2-cyclohexandiamine-N,N']-platinum (II)-diaquo-sulfate and silver chloride (AgCl),
   c1) reacting the[(trans-l-1,2-cyclohexandiamine-N,N']-platinum(II)-diaquo-sulfate with equimolar portions of barium hydroxide ($Ba(OH)_2$) and oxalic acid ($H_2C_2O_4$) to obtain oxaliplatin(cis-oxalato-(trans-l-1,2-cyclohexane-diamine)-platinum-II) and barium sulfate ($BaSO_4$).

3. The process according to claim 1, further comprising a step b') for the removal of silver chloride.

4. The process according to claim 1, further comprising a step c') for the removal of barium sulfate.

5. The process according to claim 1, further comprising a step d) for the isolation and/or purification of the oxaliplatin product.

6. The process according to claim 1, wherein after addition of barium oxalate ($BaC_2O_4$) the pH is adjusted to the range of pH=4-7.

7. The process according to claim 2, wherein after addition of oxalic acid ($H_2C_2O_4$) and barium hydroxide ($Ba(OH)_2$) the pH is adjusted to the range of pH=4-7.

8. The process according to claim 2, wherein in step c1) the barium oxalate ($BaC_2O_4$) is formed in situ in the reaction mixture.

9. The process according to claim 3, wherein the removal of silver chloride (AgCl) in step b') is performed by filtration.

10. The process according to claim 5, wherein the isolation and/or purification of the oxaliplatin product in step d) is performed by solvent evaporation.

11. The process according to claim 1, wherein after addition of barium oxalate ($BaC_2O_4$) the pH is adjusted to the range of pH=5-6.5.

12. The process according to claim 2, wherein after addition of oxalic acid ($H_2C_2O_4$) and barium hydroxide ($Ba(OH)_2$) the pH is adjusted to the range of pH=5-6.5.

13. The process according to claim 4, wherein the removal of barium sulfate ($BaSO_4$) in step c') is performed by filtration.

* * * * *